United States Patent [19]

Camenzind

[11] Patent Number: 4,965,005
[45] Date of Patent: Oct. 23, 1990

[54] AMINOMETHYL DERIVATIVES OF MONOTHIOCARBAMATES AND DITHIOCARBAMATES AS ADDITIVES FOR LUBRICANTS

[75] Inventor: Hugo Camenzind, Fribourg, Switzerland

[73] Assignee: Ciba-Geigy Corporation, Ardsley, N.Y.

[21] Appl. No.: 242,832

[22] Filed: Sep. 12, 1988

[30] Foreign Application Priority Data

Sep. 17, 1987 [CH] Switzerland ............ 3589/87

[51] Int. Cl.[5] .............. C10M 135/18; C10M 135/14
[52] U.S. Cl. .................... 252/47; 252/47.5; 252/78.1
[58] Field of Search .............. 252/47, 47.5, 78.1

[56] References Cited

U.S. PATENT DOCUMENTS

| | | |
|---|---|---|
| 3,068,098 | 12/1962 | Williams . |
| 3,081,170 | 3/1963 | Rauch et al. ............ 548/189 |
| 4,061,637 | 12/1977 | Manghisi et al. ............ 548/189 |
| 4,148,800 | 4/1979 | Schubart et al. . |
| 4,287,350 | 9/1981 | Hüllstrung et al. ............ 548/189 |
| 4,543,318 | 9/1985 | Maeda et al. . |
| 4,734,210 | 3/1988 | Camenzind et al. . |
| 4,737,302 | 4/1988 | Camenzind et al. . |
| 4,803,001 | 2/1989 | Camenzind et al. ............ 252/47 |
| 4,810,399 | 3/1989 | Camenzind et al. ............ 252/47 |

FOREIGN PATENT DOCUMENTS

1569730  6/1980  United Kingdom .

OTHER PUBLICATIONS

Fulop et al., Synthesis 1149-1151 (1985).

*Primary Examiner*—O. Chaudhuri
*Assistant Examiner*—Jerry D. Johnson
*Attorney, Agent, or Firm*—Stephen V. O'Brien

[57] ABSTRACT

Composition containing one or more lubricants or hydraulic oils based on mineral oil, synthetic oils or mixtures thereof and at least one compound of the formulae I, II or III,

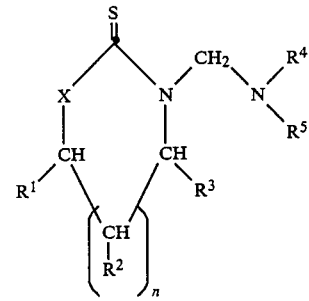

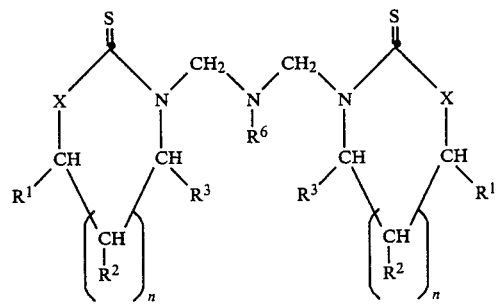

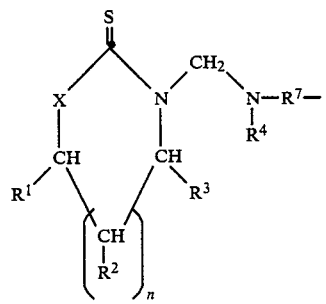

(Abstract continued on next page.)

-continued

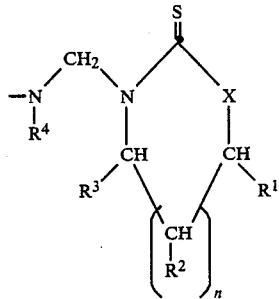

in which $R^1$, $R^2$, $R^3$, $R^4$, $R^5$ and $R^6$ independently of one another are $C_1$–$C_{24}$ alkyl or $C_1$–$C_{24}$ alkyl which can be substituted by oxo or thio groups, or $C_3$–$C_{24}$ alkyl which can be interrupted by

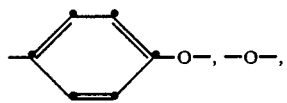

—S— and/or —N($R^8$)— in which $R^8$ is hydrogen or $C_1$–$C_{12}$ alkyl and which can be substituted by oxo or thiono groups, or $C_2$–$C_{24}$ alkenyl or phenyl or naphthyl which is unsubstituted or substituted by one or two $C_1$–$C_{12}$ alkyl, $C_2$–$C_{24}$ carboalkoxy or nitro groups; or are $C_7$–$C_{10}$ phenylalkyl, and $R^1$, $R^2$, $R^3$ and $R^4$ additionally are hydrogen, or $R^1$ and $R^2$, or $R^1$ and $R^3$ in the event that n is zero, together with the C atoms to which they are attached, form a 5-membered or 6-membered aliphatic ring which can be interrupted by —N($R^8$)— in which $R^8$ is as defined above, —O— or —S— and/or can be substituted by oxo or thiono groups; or in which $R^4$ and $R^5$, together with the N atom to which they are attached, form a 5-membered or 6-membered aliphatic-heterocyclic ring which, additionally to the N atom, can contain further heteroatoms [N($R^8$), O or S] and/or can be substituted by oxo or thiono groups, and in which $R^7$ is also $C_2$–$C_{12}$ alkylene which can be interrupted by —N($R^8$)—, —O— and/or —S— and/or can contain oxo or thiono groups, $C_6$–$C_{15}$ cycloalkylene, $C_6$–$C_{15}$ arylene, carbonyl or thiocarbonyl, or the group —N($R^4$)—$R^7$—N($R^4$)— is a piperazine-1,4-diyl radical which can be substituted by one or more methyl groups, and X is also oxygen or sulfur and n is the numbers zero or 1, and also the compounds themselves, provided that they are novel.

21 Claims, No Drawings

AMINOMETHYL DERIVATIVES OF MONOTHIOCARBAMATES AND DITHIOCARBAMATES AS ADDITIVES FOR LUBRICANTS

The present invention relates to compositions of lubricants or hydraulic oils containing oil-soluble derivatives of monothiocarbamates and dithiocarbamates, to the use of such derivatives as additives for lubricants and to the compounds themselves, insofar as they are novel.

It is customary to add additives to mineral and synthetic lubricants in order to improve their properties in use. High-pressure and wear-reducing additives are added to the lubricants in order to improve the anti-wear properties. It is a requirement for these additives that they should not have a corroding effect on the metal parts to be lubricated and should display a good stability to heat.

Compounds containing phosphorus and sulfur are preferably used nowadays for this purpose, for example dialkyl dithiophosphates according to German Offenlegungsschrift No. 2,921,620. In view of the use of catalysts in the exhaust system of combustion engines, the phosphorus content of lubricating oils should be kept as low as possible, so that the catalysts are not deactivated (H. S. Gandhi et al., Applied Catalysis 3 (1982), 79–88).

Phosphorus-free additives for lubricants, such as aminomethyl derivatives of benzothiazolinethione, are described in EP-A No. 203,033 or such as N,N-disubstituted S-thiiranylmethylcarbamothioates in EP-A No. 211,806.

A process for the preparation of thiazoline-2-thiones and the use thereof as vulcanization accelerators for polychloroprene rubbers is also described in DE-A No. 2,701,215. In Synthesis (1985) 1149–51, F. Fülöp et al. describe a method for the preparation of 2-thioxotetrahydro-1,3-oxazole and 2-thioxotetrahydro-1,3-oxazine.

Aminomethyl derivatives of thiazoline-2-thione and oxazoline-2-thione are also known from U.S. Pat. No. 3,068,098 and U.S. Pat. No. 4,543,318 as adhesion promoters for emulsions on photographic paper and as adhesion promoters for photoresists on copper substrates.

It has now been found that oil-soluble aminomethyl derivatives of cyclic monothiocarbamates and dithiocarbamates exhibit, in mineral and synthetic lubricants, excellent properties with regard to protection against frictional wear, load-carrying capacity, protection of metal parts from corrosion and freedom from ash.

The present invention therefore relates to a composition containing one or more lubricants or hydraulic oils based on mineral oil, synthetic oils or mixtures thereof and at least one compound of the formulae I, II and/or III,

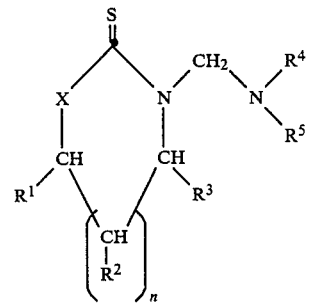

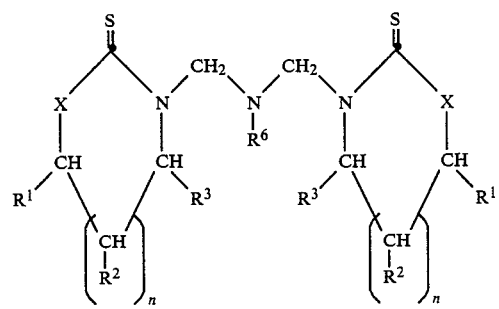

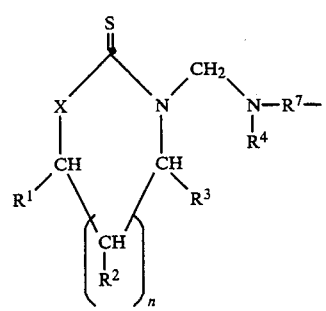

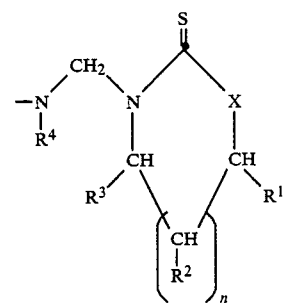

in which $R^1$, $R^2$, $R^3$, $R^4$, $R^5$ and $R^6$ independently of one another are $C_1$–$C_{24}$alkyl or $C_1$–$C_{24}$alkyl which is substituted by oxo or thiono groups or $C_3$–$C_{24}$alkyl which is interrupted by

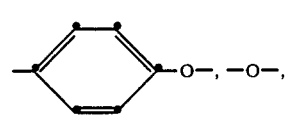 —O—, —O—,

—S— and/or —N($R^8$)— in which $R^8$ is hydrogen or $C_1$–$C_{12}$alkyl, or $C_3$–$C_{24}$alkyl which is interrupted by

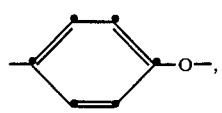

—O—, —S— and/or —N(R$^8$)— in which R$^8$ is hydrogen or C$_1$–C$_{12}$alkyl, and which is substituted by oxo or thiono groups, or C$_2$–C$_{24}$alkenyl, or phenyl or naphthyl which is unsubstituted or is substituted by one or two C$_1$–C$_{12}$alkyl, C$_1$–C$_4$alkoxy, C$_2$–C$_{24}$carboalkoxy or nitro groups, or are C$_7$–C$_{10}$phenylalkyl, and R$^1$, R$^2$, R$^3$ and R$^4$ additionally are hydrogen, or R$^1$ and R$^2$, or R$^1$ and R$^3$ in the event that n is zero, together with the C atoms to which they are attached, form a 5-membered or 6-membered aliphatic ring or form a 5-membered or 6-membered aliphatic ring which is substituted by oxo or thiono groups, or form a 5-membered or 6-membered aliphatic ring which is interrupted by —N(R$^8$)— in which R$^8$ is as defined above, —O— or —S—, or form a 5-membered or 6-membered aliphatic ring which is interrupted by —N(R$^8$)— in which R$^8$ is as defined above, —O— or —S— and is substituted by oxo or thiono groups, or in which R$^4$ and R$^5$, together with the N atom to which they are attached, form a 5-membered to 7-membered aliphatic-heterocyclic ring, or in which R$^4$ and R$^5$, together with the N atom to which they are attached, form a 5-membered to 7-membered aliphatic-heterocyclic ring and the ring is substituted by oxo or thiono groups and/or contains, additionally to the N atom, further hetero atoms [N(R$^8$), O or S] and in which R$^7$ is C$_2$–C$_{12}$alkylene, C$_2$–C$_{12}$alkylene which is interrupted by —N(R$^8$)—, —O— and/or —S—, C$_2$–C$_{12}$alkylene which contains oxo or thiono groups or C$_2$–C$_{12}$alkylene which is interrupted by —N(R$^8$)—, —O— and/or —S— and contains oxo or thiono groups, C$_6$–C$_{15}$cycloalkylene, C$_6$–C$_{15}$arylene, carbonyl or thiocarbonyl, or the group —N(R$^4$)—R$^7$—N(R$^4$)— is a piperazine-1,4-diyl radical or a piperazine-1,4-diyl radical which is substituted by one or more methyl groups, and X is oxygen or sulfur and n is the number zero or 1.

As C$_1$–C$_{24}$alkyl, R$^1$, R$^2$, R$^3$, R$^4$, R$^5$ and R$^6$ are linear or branched alkyl radicals, for example methyl, ethyl, n-propyl, isopropyl, sec-butyl, tert-butyl, linear or branched pentyl, hexyl, heptyl, octyl, 2-ethylhexyl, nonyl, decyl, undecyl, dodecyl, tridecyl, tetradecyl, pentadecyl, hexadecyl, heptadecyl, octadecyl, eicosyl, heneicosyl, docosyl, tricosyl and tetracosyl.

If R$^1$, R$^2$, R$^3$, R$^4$, R$^5$ and R$^6$ are C$_3$–C$_{24}$alkyl which is interrupted by

—O—, —S— or —N(R$^8$)—, the hetero atom or the

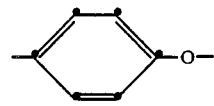

group can be located in any possible position and the C$_3$–C$_{24}$alkyl radical can be interrupted one or more times, it being possible for the interruption to be either by identical or different hetero atoms and by

groups. One interruption is preferred, however. The respective number of C-Atoms expresses the total number of members of the rest.

If R$^1$, R$^2$, R$^3$, R$^4$, R$^5$ and R$^6$ are C$_1$–C$_{24}$alkyl which is substituted by oxo or thiono groups, the alkyl radical can be substituted one or more times in any possible position, identical or different substituents being possible. In particular, an oxo substituent at a C atom which is located immediately next to an O interruption of the alkyl chain is possible, so that a C(O)—O— group is formed.

As C$_2$–C$_{24}$alkenyl, R$^1$, R$^2$, R$^3$, R$^4$, R$^5$ and R$^6$ are linear or branched alkenyl radicals containing one or more double bonds, but preferably one double bond, for example vinyl, allyl, n-butenyl, 1,3-butadienyl, i-pentenyl, pentenyl, hexenyl, heptenyl, octenyl, nonenyl, decenyl, undecenyl, dodecenyl, tridecenyl, 2-nonyl-2-butenyl, tetradecenyl, pentadecenyl, hexadecenyl and 8-heptadecenyl, 2-octadecenyl, oleyl, nonadecenyl, eicosenyl, heneicosenyl, docosenyl, tricosenyl and tetracosenyl. Allyl and oleyl are preferred.

If R$^1$, R$^2$, R$^3$, R$^4$, R$^5$ and R$^6$ are phenyl or naphthyl which is substituted by C$_1$–C$_{12}$alkyl, the phenyl or naphthyl radical can be monosubstituted or disubstituted, but preferably monosubstituted; examples of C$_1$–C$_{12}$alkyl are methyl, ethyl, n-propyl, isopropyl, n-butyl, isobutyl, sec-butyl, tert-butyl or linear or branched octyl, nonyl or dodecyl.

If R$^1$, R$^2$, R$^3$, R$^4$, R$^5$ and R$^6$ are phenyl or naphthyl which is substituted by C$_1$–C$_4$alkoxy, the phenyl or naphthyl radical can be monosubstituted or disubstituted, but preferably monosubstituted; examples of C$_1$–C$_4$alkoxy are methoxy, ethoxy, n-propoxy, isopropoxy, n-butoxy, isobutoxy, sec-butoxy or tert-butoxy.

If R$^1$, R$^2$, R$^3$, R$^4$, R$^5$ and R$^6$ are phenyl or naphthyl which is substituted by C$_2$–C$_{24}$carboalkoxy, the phenyl or naphthyl radical can be monosubstituted or disubstituted, but preferably monosubstituted; C$_2$–C$_{24}$carboalkoxy contains 1–23 carbon atoms in the alkyl moiety and can be, for example, carbomethoxy, carboethoxy, carbopropoxy or carbo-2-ethylhexyloxy.

If R$^1$, R$^2$, R$^3$, R$^4$, R$^5$ and R$^6$ are phenyl or naphthyl which is substituted by nitro, the phenyl or naphthyl radical can be monosubstituted or disubstituted, but preferably monosubstituted.

As C$_7$–C$_{10}$phenylalkyl, R$^1$, R$^2$, R$^3$, R$^4$, R$^5$ and R$^6$ are, for example, benzyl, 1-phenethyl, 2-phenethyl, 3-phenylpropyl, α,α-dimethylbenzyl or 2-phenylisopropyl, but are preferably benzyl.

If R$^1$ and R$^2$ or R$^1$ and R$^3$, together with the C atoms to which they are attached, are a 5-membered or 6-membered aliphatic ring which is interrupted by —N(R$^8$)—, —O— or —S— and/or is substituted by oxo or thiono groups, R$^1$ and R$^2$ or R$^1$ and R$^3$ together form, for example, the groups 2-oxobut-1,4-diyl, 2-oxabut-1,4-diyl, 2-thiabut-1,4-diyl, 2-thionoprop-1,3-diyl, 2-(methylaza)-but-1,4-diyl or 2-oxo-3-oxabut-1,4-diyl.

If $R^4$ and $R^5$, together with the N atom to which they are attached, are a 5-membered to 7-membered aliphatic-heterocyclic ring which, in addition to the N atom, also contains further hetero atoms [$N(R^8)$, O and S] and/or is substituted by oxo or thiono groups, they form, for example, a piperidine, perhydroazepine, piperazine, 4-methylpiperazine, morpholine, piperidin-2-one or piperidine-2-thione ring. A piperidine, perhydroazepine or morpholine ring is preferred.

As $C_2-C_{12}$alkylene, $R^7$ is a linear or branched alkylene radical, for example ethylene, propylene, trimethylene, tetramethylene, 2,2-dimethyl-1,3-trimethylene, hexamethylene, heptamethylene, octamethylene or dodecamethylene.

If $R^7$ is $C_2-C_{12}$alkylene which is interrupted by $-N(R^8)-$, $-O-$ and/or $-S-$, this can be mono-interrupted or poly-interrupted, but preferably mono-interrupted, for example 2-oxa-1,3-propylene, 2,4-dioxa-1,5-pentylene, 3,5-dioxa-1,6-hexylene, 3-oxa-1,6-hexylene, 2,5,8-trioxa-1,9-nonylene, 2,5,8-otrioxa-1,11-undecylene, 2-thia-1,3-propylene, 2,4-dithia-1,5-pentylene, 2,5,8-trithia-1,11-undecylene, 3-(methylaza)-1,5-pentylene or 3,6-di(methylaza)-1,11-undecylene.

As $C_6-C_{15}$cycloalkylene, $R^7$ is, for example, cyclo-1,4-hexylene, cyclo-1,5-octylene, cyclo-1,4-dodecylene or cyclo-1,5-pentadecylene.

As $C_6-C_{15}$arylene, $R^7$ is, for example, 1,4-phenylene, 1,3-phenylene, 2,3-naphthylene, 1,5-naphthylene, 1,8-naphthylene, 9,10-anthracenylene, 9,10-phenanthrenylene or 4,4'-biphenylylene. 1,4-phenylene, 2,3-naphthylene and 4,4'-biphenylylene, in particular 4,4'-biphenylylene, are preferred.

As $C_1-C_{12}$alkyl, $R^8$ is a linear or branched alkyl radical, for example methyl, ethyl, n-propyl, isopropyl, n-butyl, isobutyl, sec-butyl, tert-butyl, linear or branched pentyl, hexyl, heptyl, octyl, nonyl, decyl, undecyl or dodecyl. Methyl, ethyl, n-propyl, isopropyl, n-butyl, isobutyl, sec-butyl and tert-butyl are preferred, in particular methyl.

A composition wherein, in the compounds of the formulae I, II or III, n is 1 is preferred.

A composition wherein, in the compounds of the formulae I, II or III, $R^2$ is hydrogen, $C_1-C_{12}$alkyl, phenyl or benzyl is particularly preferred.

A composition wherein, in the compounds of the formulae I, II or III, $R^1$ and $R^2$, together with the C atoms to which they are attached, form a 6-membered aliphatic ring is especially preferred.

A composition wherein, in the compounds of the formulae I, II or III, n is zero is also preferred.

A composition wherein, in the compounds of the formulae I, II or III, $R^1$ is hydrogen, $C_1-C_{12}$alkyl which can be substituted by an oxo group, $C_3-C_{12}$alkyl which is interrupted by

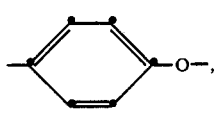

$-O-$ or $-S-$ and which can be substituted by an oxo group, phenyl or benzyl is also preferred.

A composition wherein, in the compounds of the formulae I, II or III, $R^3$ is hydrogen or $C_1-C_4$alkyl, but preferably hydrogen, is particularly preferred.

A composition wherein, in the compounds of the formulae I, II or III, $R^1$ and $R^3$ are hydrogen is very particularly preferred.

A composition wherein, in the compounds of the formulae I or III, $R^4$ is hydrogen, $C_1-C_{12}$alkyl, $C_3-C_{18}$alkenyl, phenyl or benzyl, but particularly hydrogen or $C_1-C_8$alkyl, is also of interest.

A composition wherein, in the compound of the formula I, $R^5$ is $C_1-C_{18}$alkyl, $C_3-C_{18}$alkenyl, phenyl or benzyl, but particularly $C_4-C_{18}$alkyl, oleyl or phenyl, is also of interest.

A composition wherein, in the compound of the formula I, $R^4$ and $R^5$, together with the N atom to which they are attached, form a piperidine, perhydroazepine, morpholine, piperazine or a 4-N-methylpiperazine ring, but particularly a piperidine or morpholine ring, are of particular interest.

A composition wherein, in the compound of the formula II, $R^6$ is $C_1-C_{12}$alkyl, $C_3-C_{18}$alkenyl, phenyl or benzyl, but particularly oleyl or benzyl and very particularly oleyl, is also of interest.

A composition wherein, in the compound of the formula III, $R^7$ is 4,4'-biphenylylene is also of interest.

A composition wherein, in the compound of the formula III, the group $-N(R^4)-R^7-N(R^4)-$ is piperazine-1,4-diyl is also of interest.

A composition wherein, in the compounds of the formulae I, II or III, X is sulfur is of particular interest.

Compositions containing at least one compound of the formulae

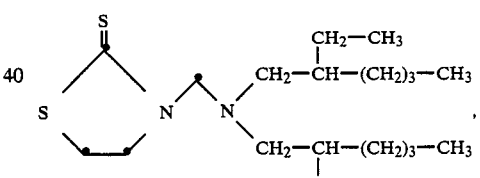

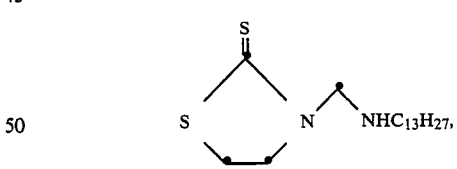

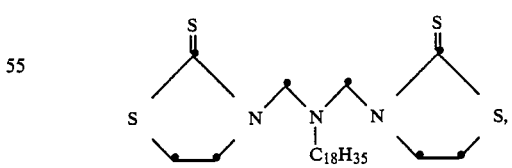

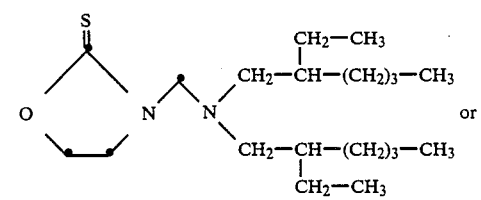

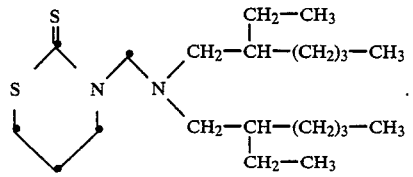

are very particularly preferred.

A composition wherein at least one compound of the formulae I or II, but preferably at least one compound of the formula I, is present as the additive is a further embodiment.

A composition wherein, in the compounds of the formulae I and II, n is zero, $R^1$ and $R^3$ are hydrogen, $R^4$ and $R^5$ independently of one another are $C_1$–$C_{18}$alkyl or $C_3$–$C_{18}$alkenyl and $R^6$ is $C_3$–$C_{18}$alkenyl and X is sulfur is an especially preferred embodiment.

The following are examples of compounds of the formulae I, II or III: 3-dibutylaminomethylthiazolidine-2-thione, 3-[(di-2-ethylhexyl)aminomethyl]-thiazolidine-2-thione, 3-tridecylaminomethylthiazolidine-2-thione, 3-oleylaminomethylthiazolidine-2-thione, 3-[n-Phenyl-N-methylaminomethyl]-5-[tert-butylthiomethyl]-thiazolidine-2-thione, 3-piperidinomethyl-5-acetoxymethyloxazolidine-2-thione, 3-morpholinomethyl-5,6-tetramethyleneperhydrooxazine-2-thione, 3-di-tert-dodecylmethylamino-4-methyl-5-butylthiazolidine-2-thione, 3-dibutylaminomethyl-5-vinyloxazolidine-2-thione, 3-(4-oxaoctyl)aminomethyl-thiazolidine-2-thione, bis-[(2-thionooxazolidino)methyl]-benzylamine, bis-[(2-thionothiazolidino)methyl]-oleylamine bis-[(2-thiono-5-isopropyl-oxazolidino)methyl]-aniline, bis-[(2-thiono-5-methylthiazolidino)methyl]-butylamine, ethylene-N,N'-[bis(2-thiono-5,6-dimethylperhydrooxazino)-methyl]-N,N'-dibutyldiamine, 4,4'-biphenylylene-N,N'-[bis-(2-thionothiazolidino)methyl]-diamine and 1,4-bis[(2-thiono-5-(4'-nonylphenoxymethyl)-thiazolidino)methyl]-piperazine.

The compounds of the formulae I, II and III are in part known and in part novel. 3-Dimethylaminomethyl-5-phenyloxazolidine-2-thione, 3-cyclohexylaminomethyl-5-methyloxazolidine-2-thione, 3-piperidinomethyl-5-methyloxazolidine-2-thione, 3-piperidinomethyloxazolidine-2-thione, 3-morpholinomethyl-5-methyloxazolidine-2-thione, 3-morpholinomethyl-4-methyloxazolidine-2-thione, 3-morpholinomethyloxazolidine-2-thione, 3-[(4'-methylpiperazino)methyl]-5-methyloxazolidine-2-thione, 3-dimethylaminomethylthiazolidine-2-thione, 3-diethylaminomethylthiazolidine-2-thione, 3-piperidinomethylthiazolidine-2-thione, 3-morpholinomethyl-5-methylthiazolidine-2-thione, 3-morpholinomethyl-4-methylthiazolidine-2-thione, 3-morpholinomethyl-5-phenylthiazolidine-2-thione, 3[(4'-methylpiperazino)methyl]-thiazolidine-2-thione, bis-[(2-thiono-5-methyloxazolidino)methyl]-methylamine, bis-[(2-thiono-5-methyloxazolidino)methyl]-isopropylamine and bis[(2-thionothiazolidino)methyl]-methylamine are known.

The present invention therefore also relates to compounds of the formulae I*, II* and III*

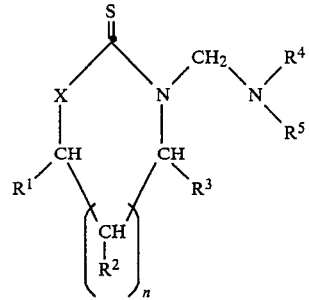

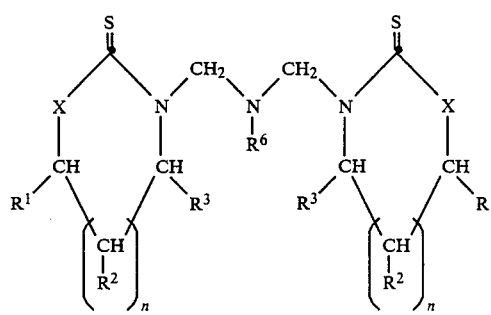

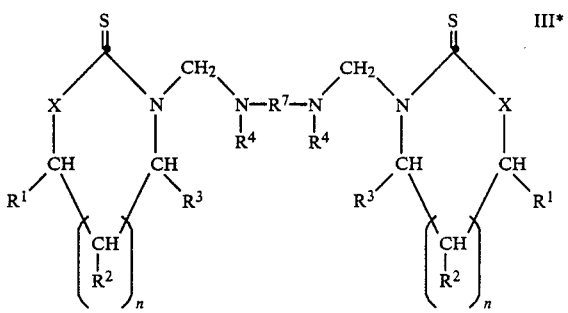

in which $R^1$, $R^2$, $R^3$, $R^4$, $R^5$ and $R^6$ independently of one another are $C_1$–$C_{24}$alkyl or $C_1$–$C_{24}$alkyl which is substituted by oxo or thiono groups or $C_3$–$C_{24}$alkyl which is interrupted by

—O—, —S— and/or —N($R^8$)— in which $R^8$ is hydrogen or $C_1$–$C_{12}$alkyl or $C_3$–$C_{24}$alkyl which is interrupted by

—O—, —S— and/or —N($R^8$)— in which $R_8$ is hydrogen or $C_1$–$C_{12}$alkyl, and which is substituted by oxo or thiono groups, or $C_2$–$C_{24}$-alkenyl, or phenyl or naphthyl which is unsubstituted or substituted by one or two $C_1$–$C_{12}$alkyl, $C_1$–$C_4$alkoxy, $C_2$–$C_{24}$carboalkoxy or nitro groups, or are $C_7$–$C_{10}$phenylalkyl, and $R^1$, $R^2$, $R^3$ and $R^4$ additionally are hydrogen, or $R^1$ and $R^2$, or $R^1$ and $R^3$ in the event that n is zero, together with the C atoms to which they are attached, form a 5-membered or 6- membered aliphatic ring or form a 5-membered or 6-membered aliphatic ring which is substituted by oxo or thiono groups or form a 5-membered or 6-membered aliphatic ring which is interrupted by —N(R$^8$)— in which R$^8$ is as defined above, —O— or —S—, or form a 5-membered or 6-membered aliphatic ring which is interrupted by —N(R$^8$)— in which R$^8$ is as defined above, —O— or —S— and is substituted by oxo or thiono groups, or in which R$^4$ and R$^5$, together with the N atom to which they are attached, form a 5-membered to 7-membered aliphatic-heterocyclic ring, or in which R$^4$ and R$^5$, together with the N atom to which they are attached, form a 5-membered to 7-membered aliphatic-heterocyclic ring and the ring is substituted by oxo or thiono groups and/or contains, additionally to the N atom, further hereto atoms [N(R$^8$). O or S], and in which R$^7$ is C$_2$-C$_{12}$alkylene, C$_2$-C$_{12}$alkylene which is interrupted by —N(R$^8$)—, —O— and/or —S—, C$_2$-C$_{12}$alkylene which contains oxo or thiono groups, C$_6$-C$_{15}$cycloalkylene, C$_6$-C$_{15}$arylene, carbonyl or thiocarbonyl, or the group —N(R$^4$)—R—N(R$^4$)— is a piperazine-1,4-diyl radical which can be substituted by one ore more methyl groups, and X is also oxygen or sulfur and n is the number zero or 1, subject to the proviso that the compounds listed above as known are not embraced.

With regard to the preferences for specific compounds of the formulae I*, II* and III*, the same preferences as those which have been defined for the components of the formulae I, II and III in the compositions of lubricants or hydraulic oils apply analogously.

The following compounds are very particularly preferred

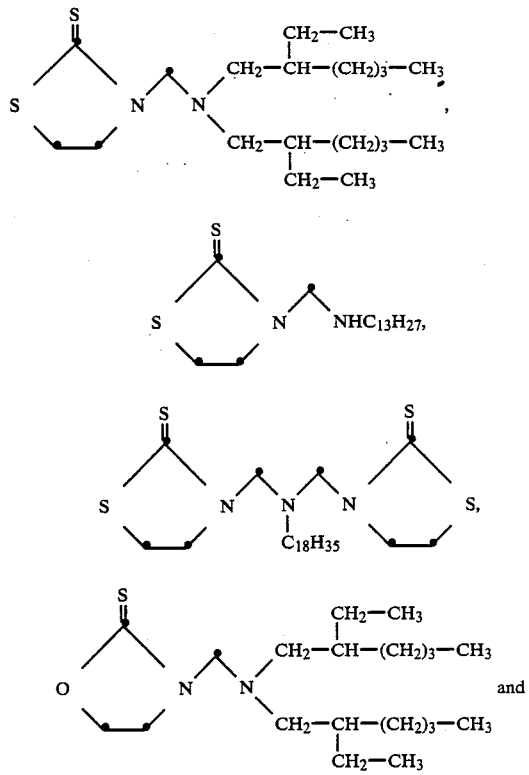

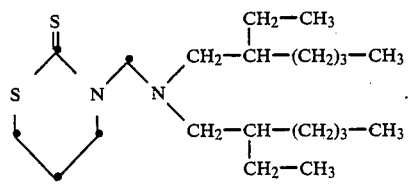

The preparation of the compounds of the formula I, II or III is effected in a manner known per se.

Thus, for example, the heterocyclic rings, such as oxazolidine-2-thione or perhydrooxazine-2-thione, can be prepared by the method described in Fülöp et al in Synthesis (1985) 1149–51.

Thiazolidine-2-thione and derivatives thereof can, for example, be prepared by the process described in DE-A No. 2,701,215.

Perhydrothiazine-2-thione and derivatives thereof can, for example, be prepared by the method described in U.S. Pat. No. 2,920,996.

The aminomethyl derivatives according to the invention are prepared in a customary manner by a Mannich reaction between the heterocyclic compounds mentioned above and formaldehyde and a primary or secondary amine.

The compounds of the formula II are prepared analogously using formaldehyde and a primary amine, the molar ratio of heterocyclic compound:formaldehyde:amine being 2:2:1.

The compounds of the formula III are prepared by a Mannich reaction between the heterocyclic compounds and formaldehyde and a primary or secondary diamine, the molar ratio of heterocyclic compound:formaldehyde:amine being 2:2:1.

The compounds of the formulae I, II or III are excellently suitable for use as anti-wear additives and high-pressure additives for lubricants and hydraulic oils, preferably for lubricants.

The present invention also relates, therefore, to the use of at least one compound of the formulae I, II or III as high-pressure additives or wear-reducing additives for mineral or synthetic lubricants or hydraulic oils.

The compounds of the formulae I, II or III are soluble to an adequate extent in lubricants and hydraulic oils and are employed, for example, in a concentration of 0.05 to 5% by weight, preferably in a concentration of 0.1 to 3% by weight, relative to the total weight of the lubricant or hydraulic oil composition.

Suitable lubricants or hydraulic oils are familiar to those skilled in the art and are described, for example, in "Schmiermittel Taschenbuch" ["Manual of Lubricants"] (Hüthig Verlag, Heidelberg, 1974) or in "Ullmanns Encyclopädie der technischen Chemie" [Ullmann's Encyclopaedia of Industrial Chemistry"] Volume 13, pages 85–94 (Verlag Chemie, Weinheim 1977).

In addition to mineral oils, particularly suitable examples of these products are poly-α-olefins, lubricants based on esters, phosphate esters, glycols, polyglycols and polyalkylene glycols.

The lubricants can additionally contain other additives which are added in order to improve the fundamental properties of lubricants and hydraulic oils still further; these include antioxidants, metal passivators, rust inhibitors, viscosity index improvers, setting point depressants, dispersing agents, detergents, other high-pressure additives and other anti-wear additives.

Examples of phenolic antioxidants
1. Alkylated monophenols
2,6-Ditert-butyl-4-methylphenol
2,6-Ditert-butylphenol
2-Tert-butyl-4,6-dimethylphenol
2,6-Ditert-butyl-4-ethylphenol
2,6-Ditert-butyl-4-isopropylphenol
2,6-Ditert-butyl-4-n-butylphenol
2,6-Ditert-butyl-4-isobutylphenol
2,6-Dicyclopentyl-4-methylphenol
2-(α-Methylcyclohexyl)-4,6-dimethylphenol
2,6-Dioctadecyl-4-methylphenol
2,4,6-Tricyclohexylphenol
2,6-Ditert-butyl-4-methoxymethylphenol
o-Tert-butylphenol
2. Alkylated hydroquinones
2,6-Ditert-butyl-4-methoxyphenol
2,5-Ditert-butylhydroquinone
2,5-Ditert-amylhydroquinone
2,6-Diphenyl-4-octadecyloxyphenol
3. Hydroxylated thiodiphenyl ethers
2,2'-Thiobis-(6-tert-butyl-4-methylphenol)
2,2'-Thiobis-(4-octylphenol)
4,4'-Thiobis-(6-tert-butyl-3-methylphenol)
4,4'-Thiobis-(6-tert-butyl-2-methylphenol)
4. Alkylidene bisphenols
2,2'-Methylenebis-(6-tert-butyl-4-methylphenol)
2,2'-Methylenebis-(6-tert-butyl-4-ethylphenol)
2,2'-Methylenebis-[4-methyl-6-(α-methylcyclohexyl)-phenol]
2,2'-Methylenebis-(4-methyl-6-cyclohexylphenol)
2,2'-Methylenebis-(6-nonyl-4-methylphenol)
2,2'-Methylenebis-(4,6-ditert-butylphenol)
2,2'-Ethylidenebis-(4,6-ditert-butylphenol)
2,2'-Ethylidenebis-(6-tert-butyl-4-isobutylphenol)
2,2'-Methylenebis-[6-(α-methylbenzyl)-4-nonylphenol]
2,2'-Methylenebis-[6-(α,α-dimethylbenzyl)-4-nonylphenol]
4,4'-Methylenebis-(2,6-ditert-butylphenol)
4,4'-Methylenebis-(6-tert-butyl-2-methylphenol)
1,1-Bis-(5-tert-butyl-4-hydroxy-2-methylphenyl)-butane
2,6-Di-(3-tert-butyl-5-methyl-2-hydroxybenzyl)-4-methylphenol
1,1,3-Tris-(5-tert-butyl-4-hydroxy-2-methylphenyl)-3-n-dodecylmercaptobutane
Ethylene glycol bis-[3,3-bis-(3'-tert-butyl-4'-hydroxyphenyl)-butyrate]
Di-(3-tert-butyl-4-hydroxy-5-methylphenyl)-dicyclopentadiene
Di[2-(3'-tert-butyl-2'-hydroxy-5'-methylbenzyl)-6-tert-butyl-4-methylphenyl] terephthalate
5. Benzyl compounds
1,3,5-Tri-(3,5-ditert-butyl-4-hydroxybenzyl)-2,4,6-trimethylbenzene
Di-(3,5-ditert-butyl-4-hydroxybenzyl) sulfide
Isooctyl 3,5-ditert-butyl-4-hydroxybenzylmercapto acetate
Bis-(4-tert-butyl-3-hydroxy-2,6-dimethylbenzyl)-dithiol terephthalate
1,3,5-Tris-(3,5-ditert-butyl-4-hydroxybenzyl) isocyanurate
1,3,5-Tris-(4-tert-butyl-3-hydroxy-2,6-dimethylbenzyl) isocyanurate
Dioctadecyl 3,5-ditert-butyl-4-hydroxybenzylphosphonate
Calcium salt of monoethyl 3,5-ditert-butyl-4-hydroxybenzylphosphonate
6. Acylaminophenols
4-Hydroxylauranilide
4-Hydroxystearanilide
2,4-Bis-octylmercapto-6-(3,5-ditert-butyl-4-hydroxyanilino)-s-triazine
Octyl N-(3,5-ditert-butyl-4-hydroxyphenyl)-carbamate.
7. Esters of β-(3,5-ditert-butyl-4-hydroxyphenyl)-propionic acid
with monohydric or polyhydric alcohols, for example with
Methanol
Octadecanol
1,6-Hexanediol
Neopentyl glycol
Thiodiethylene glycol
Diethylene glycol
Triethylene glycol
Pentaerythritol
Tris-hydroxyethyl isocyanurate and
Dihydroxyethyloxalic diamide
8. Esters of β-(5-tert-butyl-4-hydroxy-3-methylphenyl)-propionic acid
with monohydric or polyhydric alcohols, for example with
Methanol
Octadecanol
1,6-Hexanediol
Neopentyl glycol
Thiodiethylene glycol
Diethylene glycol
Triethylene glycol
Pentaerythritol
Tris-hydroxyethyl isocyanurate and
Dihydroxyethyloxalic diamide.
9. Amides of β-(3,5-ditert-butyl-4-hydroxyphenyl)-propionic acid
for example
N,N'-Di-(3,5-ditert-butyl-4-hydroxyphenylpropionyl)-hexamethylenediamine
N,N'-Di-(3,5-ditert-butyl-4-hydroxyphenylpropionyl)-trimethylenediamine
N,N'-Di-(3,5-ditert-butyl-4-hydroxyphenylpropionyl)-hydrazine.
Examples of aminic antioxidants:
N,N'-Diisopropyl-p-phenylenediamine
N,N'-Disec-butyl-p-phenylenediamine
N,N'-Bis-(1,4-dimethylpentyl)-p-phenylenediamine
N,N'-Bis-(1-ethyl-3-methylpentyl)-p-phenylenediamine
N,N'-Bis-(1-methylheptyl)-p-phenylenediamine
N,N'-Diphenyl-p-phenylenediamine
N,N'-Di-(2-naphthyl)-p-phenylenediamine
N-Isopropyl-N'-phenyl-p-phenylenediamine
N-(1,3-Dimethylbutyl)-N'-phenyl-p-phenylenediamine
N-(1-Methylheptyl)-N'-phenyl-p-phenylenediamine
N-Cyclohexyl-N'-phenyl-p-phenylenediamine
4-(p-Toluenesulfonamido)-diphenylamine
N,N'-Dimethyl-N,N'-disec-butyl-p-phenylenediamine Diphenylamine
4-Isopropoxydiphenylamine
N-Phenyl-1-naphthylamine
N-Phenyl-2-naphthylamine
Octylated diphenylamine
4-n-Butylaminophenol 4-Butyrylaminophenol
4-Nonanoylaminophenol
4-Dodecanoylaminophenol
4-Octadecanoylaminophenol
Di-(4-methoxyphenyl)-amine
2,6-Ditert-butyl-4-dimethylaminomethylphenol
2,4'-Diaminodiphenylmethane
4,4'-Diaminodiphenylmethane
N,N,N',N'-Tetramethyl-4,4'-diaminodiphenylmethane
1,2-Di-[(2-methylphenyl)-amino]-ethane
1,2-Di-(phenylamino)-propane
(o-Tolyl)-biguanide
Di-[4-(1',3'-dimethylbutyl)-phenyl]-amine
Tert-octylated N-phenyl-1-naphthylamino
Mixture of monoalkylated and dialkylated tert-butyl/tert-octyldiphenylamines.

The following are examples of metal passivators:
for copper, for example:
Triazole, benzotriazole and derivatives thereof, 2-mercaptobenzothiazole, 2,5-dimercaptothiadiazole, salicylidenepropylenediamine and salts of salicylaminoguanidine.

The following are examples of rust inhibitors:
(a) Organic acids, esters, metal salts and anhydrides thereof, for example: N-oleoylsarcosine, sorbitan monooleate, lead naphthenate, dodecenylsuccinic anhydride, half-esters of alkenylsuccinic acid and 4-nonylphenoxyacetic acid.
(b) Nitrogen-containing compounds, for example:
I. Primary, secondary or tertiary aliphatic or cycloaliphatic amines and amine salts of organic and inorganic acids, for example oil-soluble alkylammonium carboxylates.
II. Heterocyclic compounds, for example: substituted imidazolines and oxazolines.
(c) Phosphorus-containing compounds, for example: amine salts of partial esters of phosphoric acid.
(d) Sulfur-containing compounds, for example: barium dinonylnaphthalenesulfonates or calcium petroleumsulfonates.

The following are examples of viscosity index improvers
Polymethacrylates, vinylpyrrolidone/methacrylate copolymers, polybutenes, olefin copolymers and styrene/acrylate copolymers.

The following are examples of setting point depressants:
Polymethacrylate and alkylated naphthalene derivatives.

The following are examples of dispersing agents/surfactants:
Polybutenylsuccinic acid imides, polybutenylphosphonic acid derivatives and basic magnesium, calcium and bariumsulfonates and phenates.

The following are examples of anti-wear additives:
Compounds containing sulfur and/or phosphorus and/or halogen, such as sulfurized vegetable oils, zinc dialkyldithiophosphates, tritolyl phosphate, chlorinated paraffins and alkyl and aryl disulfides.

In the following examples, parts and percentages are by weight, unless stated otherwise.

EXAMPLE 1

3-(dibutylaminomethyl)-thiazoline-2-thione. A suspension of 47.3 g (0.4 mol) of 2-mercaptothiazoline together with 52.3 g (0.4 mol) of dibutylamine and 34.3 g (0.41 mol) of 36% aqueous formaldehyde in 150 ml of toluene is stirred for 5 hours at 50° C. The water is then separated off from the clear toluene phase and the latter is evaporated under reduced pressure. This gives 94.8 g (yield 91%) of 3-(dibutylaminomethyl)-thiazoline-2-thione in the form of a yellowish, highly fluid oil. $n_D^{20}$ 1.5512.

Examples 2–7 are prepared analogously. The results are shown in Table 1.

TABLE 1

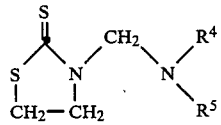

| Example | $-N\binom{R^4}{R^5}$ | Yield [%] | Appearance | $n_D^{20}$ | Analysis | C | H | N | S |
|---|---|---|---|---|---|---|---|---|---|
| 1 | $-N\binom{C_4H_9}{C_4H_9}$ | 91 | pale yellow oil | 1.5512 | Calculated found | 55.34 55.41 | 9.29 9.27 | 10.76 10.90 | 24.62 24.62 |
| 2 | $-N\binom{i\text{-}C_8H_{17}}{i\text{-}C_8H_{17}}$ | 98 | pale yellow oil | 1.5280 | calculated found | 64.46 64.65 | 10.82 10.63 | 7.52 7.60 | 17.21 16.62 |
| 3 | $-N\binom{H}{C_{13}H_{27}}$ | 93 | light yellow oil | 1.5440 | calculated found | 61.76 60.89 | 10.37 10.24 | 8.47 8.76 | 19.40 20.10 |

TABLE 1-continued (header structure showing compound with S=C(S)-N-CH2-CH2 ring and CH2-N(R4)(R5) substituent)

| Example | -N(R4)(R5) | Yield [%] | Appearance | $n_D^{20}$ | | C | H | N | S |
|---|---|---|---|---|---|---|---|---|---|
| 4 | (structure: CH2-N, CH2-CH2, -N-C18H35, with C=S, S) | | light yellow, highly viscous oil | 1.5718 | | | | | |
| 5 | (8-membered N-ring) | 98 | yellow oil | 1.6103 | calculated found | 52.13 52.26 | 7.88 7.94 | 12.16 12.14 | 27.83 27.72 |
| 6 | (morpholine-thione with branched alkyl N-substituents, CH2-CH(CH2-CH3)-(CH2)3-CH3) | 99 | pale yellow oil | 1.4988 | calculated found | 67.36 67.73 | 11.31 11.27 | 7.86 8.18 | 8.99 8.84 |
| 7 | (thiomorpholine-thione with branched alkyl N-substituents) | 98 | pale yellow oil | 1.5309 | calculated found | 65.22 65.35 | 10.95 10.81 | 7.24 7.28 | 16.58 16.48 |

EXAMPLE 8

The following values are determined using the Shell four ball apparatus (IP 239/73 Extreme pressure and wear lubricant test for oils and greases—four ball machine; ASTM-D 2783-81):

1. W.L.=weld load (in (kg)). This is the load at which the 4 balls weld together within 10 seconds.
2. W.S.D.=Wear scar diameter in (mm). This is the average wear diameter at a loading of 40 kg for 1 hour.

The base oil used is Catenex ® P 941 made by Shell. The results are shown in Table 2.

TABLE 2

| Additive from example | Concentration [%] | W.L. [kg] | W.S.D. [mm] |
|---|---|---|---|
| None | — | 160 | 0.9 |
| 1 | 1.0 | 220 | 0.60 |
|   | 2.5 | 260 | |
| 2 | 1.0 | 220 | 0.7 |
|   | 2.5 | 260 | |
| 3 | 1.0 | 240 | 0.7 |
|   | 2.5 | 260 | |
| 4 | 1.0 | 220 | 0.75 |
|   | 2.5 | 260 | |
| 5 | 1.0 | 220 | 0.70 |
| 6 | 1.0 | 200 | 0.57 |
| 7 | 1.0 | 200 | 0.75 |

What is claimed is:

1. A composition containing one or more lubricants or hydraulic oils based on mineral oil, synthetic oils or mixtures thereof and at least one compound of the formulae I, II and/or III,

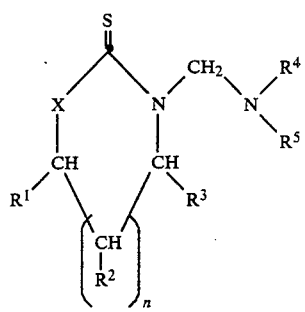

I

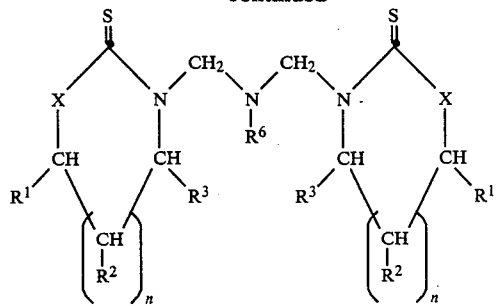

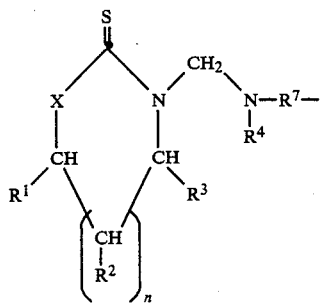

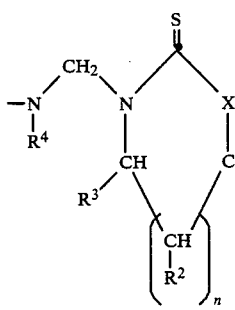

in which $R^1$, $R^2$, $R^3$, $R^4$, $R^5$ and $R^6$ independently of one another are $C_1$-$C_{24}$alkyl or $C_1$-$C_{24}$alkyl which is substituted by oxo or thiono groups or $C_3$-$C_{24}$alkyl which is interrupted by

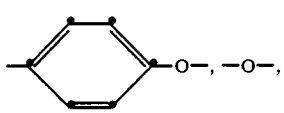

—S— and/or —N($R^8$)— in which $R^8$ is hydrogen or $C_1$-$C_{12}$alkyl, or $C_3$-$C_{24}$-alkyl which is interrupted by

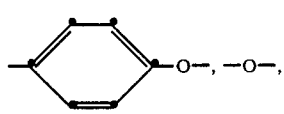

—S— and/or —N($R^8$)— in which $R^8$ is hydrogen or $C_1$-$C_{12}$alkyl, and which is substituted by oxo or thiono groups, or $C_2$-$C_{24}$alkenyl, or phenyl or naphthyl which is unsubstituted or is substituted by one or two $C_1$-$C_{12}$alkyl, $C_1$-$C_4$alkoxy, $C_2$-$C_{24}$carboalkoxy or nitro groups, or are $C_7$-$C_{10}$phenylalkyl, and $R^1$, $R^2$, $R^3$ and $R^4$ additionally are hydrogen, or $R^1$ and $R^2$, or $R^1$ and $R^3$ in the event that n is zero, together with the C atoms to which they are attached, form a 5-membered or 6-membered aliphatic ring or form a 5-membered or 6-membered aliphatic ring which is substituted by oxo or thiono groups, or form a 5-membered or 6-membered aliphatic ring which is interrupted by —N($R^8$)— in which $R^8$ is as defined above, —O— or —S—, or form a 5-membered or 6-membered aliphatic ring which is interrupted by —N($R^8$)— in which $R^8$ is as defined above, —O— or —S— and is substituted by oxo or thiono groups, or in which $R^4$ and $R^5$, together with the N atom to which they are attached, form a 5-membered to 7-membered aliphatic-heterocyclic ring, or in which $R^4$ and $R^5$, together with the N atom to which they are attached, form a 5-membered to 7-membered aliphatic-heterocyclic ring and the ring is substituted by oxo or thiono groups and/or contains, additionally to the N atom, therefor N($R^8$), O or S and in which $R^7$ is $C_2$-$C_{12}$alkylene, $C_2$-$C_{12}$alkylene which is interrupted by —N($R^8$)—, —O— and/or —S—, $C_2$-$C_{12}$alkylene which contains oxo or thiono groups or $C_2$-$C_{12}$alkylene which is interrupted by —N($R^8$)—, —O— and/or —S— and contains oxo or thiono groups, $C_6$-$C_{15}$cycloalkylene, $C_6$-$C_{15}$arylene, carbonyl or thiocarbonyl, or the group —N($R^4$)—$R^7$—N($R^4$)— is a piperazine-1,4-diyl radical or a piperazine-1,4-diyl radical which is substituted by one or more methyl groups, and X is oxygen or sulfur and n is the numbers zero or 1.

2. A composition according to claim 1, wherein, in the compounds of the formulae I, II or III, n is zero.

3. A composition according to claim 1, wherein, in the compounds of the formulae I, II or III, $R^1$ is hydrogen, $C_1$-$C_{12}$alkyl, $C_1$-$C_{12}$alkyl which is substituted by an oxo group, $C_3$-$C_{12}$alkyl which is interrupted by

—O— or —S— or $C_3$-$C_{12}$alkyl which is interrupted by

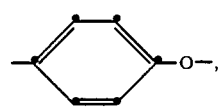

—O— or —S— and which is substituted by an oxo group, phenyl or benzyl.

4. A composition according to claim 1, wherein, in the compounds of the formulae I, II or III, $R^3$ is hydrogen or $C_1$-$C_4$alkyl.

5. A composition according to claim 4, wherein, in the compounds of the formulae I, II or III, $R^3$ is hydrogen.

6. A composition according to claim 1, wherein, in the compounds of the formulae I, II or III, $R^1$ and $R^3$ are hydrogen.

7. A composition according to claim 1, wherein, in the compounds of the formulae I or III, $R^4$ is hydrogen, $C_1$-$C_{12}$alkyl, $C_3$-$C_{18}$alkenyl, phenyl or benzyl.

8. A composition according to claim 1, wherein, in the compound of the formula I, $R^5$ is $C_1$-$C_{18}$alkyl, $C_3$-$C_{18}$alkenyl, phenyl or benzyl.

9. A composition according to claim 1, wherein, in the compound of the formula I, $R^4$ and $R^5$, together with the N atom to which they are attached, form a piperidine, perhydroazepine, morpholine, piperazine or a 4-N-methylpiperazine ring.

10. A composition according to claim 1, wherein, in the compound of the formula II, $R^6$ is $C_1$–$C_{12}$alkyl, $C_3$–$C_{18}$alkenyl, phenyl or benzyl.

11. A composition according to claim 1, wherein, in the compounds of the formulae I, II or III, X is sulfur.

12. A composition according to claim 1, wherein the amount of the compounds of the formulae I, II or III is 0.05 to 5% by weight, relative to the total weight of the composition.

13. A composition according to claim 1, containing at least one compound of the formulae I or II.

14. A composition according to claim 13, containing at least one compound of the formula I.

15. A composition according to claim 14, wherein, in the compounds of the formulae I and II, n is zero, $R^1$ and $R^3$ are hydrogen, $R^4$ and $R^5$ independently of one another are $C_1$–$C_{18}$alkyl or $C_3$–$C_{18}$alkenyl and $R^6$ is $C_3$–$C_{18}$alkenyl and X is sulfur.

16. A composition according to claim 1, containing at least one compound of the formulae

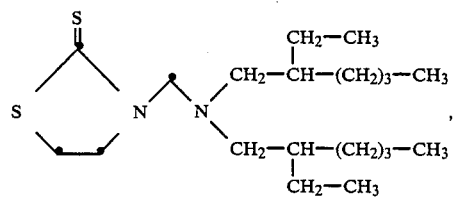
,

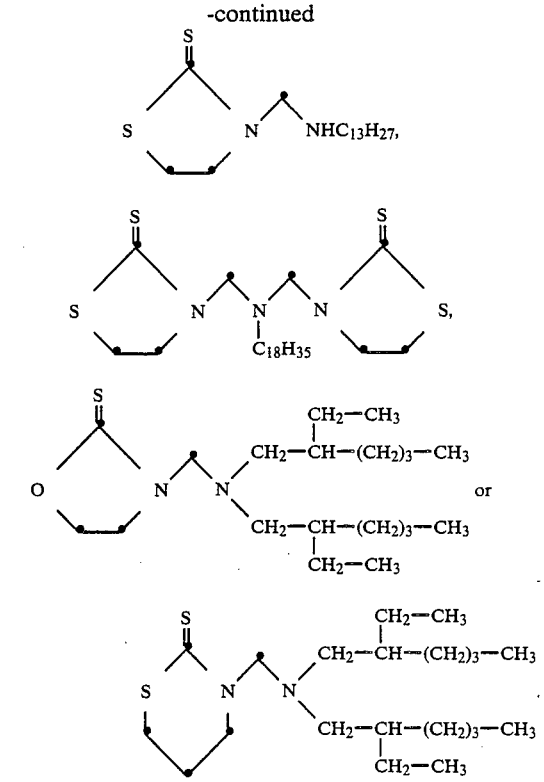

17. A composition according to claim 1, wherein, in the compounds of formulae I, II or III, n is 1.

18. A composition according to claim 17, wherein, in the compounds of formulae I, II or III, $R^2$ is hydrogen, $C_1$–$C_{12}$alkyl, phenyl or benzyl.

19. A composition according to claim 17, wherein, in the compounds of the formulae I, II or III, $R^1$ and $R^2$, together with the C atoms to which they are attached, form a 6-membered aliphatic ring.

20. A composition according to claim 1, wherein, in the compound of the formula III, $R^7$ is 4,4′-biphenylene.

21. A composition according to claim 1, wherein, in the compound of the formula III, the group —N($R^4$)—$R^7$—N($R^4$)— is piperazine-1,4-diyl.

* * * * *